(12) United States Patent
Cao et al.

(10) Patent No.: US 9,024,113 B2
(45) Date of Patent: May 5, 2015

(54) POLYNUCLEOTIDES FOR EXPRESSION OF MICROBIAL STARCH BRANCHING ENZYMES IN PLANTS FOR PRODUCTION OF PLANTS WITH IMPROVED YIELD

(75) Inventors: Yongwei Cao, Chesterfield, MO (US); Gregory J. Hinkle, Plymouth, MA (US); Steven C. Slater, Middleton, WI (US); Xianfeng Chen, Wildwood, MO (US); Barry S. Goldman, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1340 days.

(21) Appl. No.: 11/980,183

(22) Filed: Oct. 29, 2007

(65) Prior Publication Data

US 2008/0229451 A1    Sep. 18, 2008

Related U.S. Application Data

(63) Continuation of application No. 10/369,493, filed on Feb. 20, 2003, now Pat. No. 7,314,974.

(60) Provisional application No. 60/360,039, filed on Feb. 21, 2002.

(51) Int. Cl.
*C12N 15/82* (2006.01)
*A01H 5/00* (2006.01)
*C07K 14/195* (2006.01)

(52) U.S. Cl.
CPC .......... *C12N 15/8261* (2013.01); *C07K 14/195* (2013.01); *C12N 15/8241* (2013.01); *C12N 15/8243* (2013.01); *C12N 15/8273* (2013.01)

(58) Field of Classification Search
None
See application file for complete search history.

(56) References Cited

U.S. PATENT DOCUMENTS

| 5,914,451 | A | * | 6/1999 | Martinell et al. ............. 800/300 |
| 6,013,861 | A | | 1/2000 | Bird et al. |
| 6,414,221 | B1 | * | 7/2002 | Oetiker et al. ................ 800/287 |

FOREIGN PATENT DOCUMENTS

WO    WO 00/31282    *    6/2000    ............. C12N 15/82

OTHER PUBLICATIONS

Thon V. J. et al. Coordinate regulation of glycogen metabolism in the yeast *Saccharomyces cerevisiae*. Induction of glycogen branching enzyme. J Biol Chem. Jul. 25, 1992;267(21):15224-8.*
Doerks T. et al. Protein annotation: detective work for function prediction. Trends Genet. Jun. 1998;14(6):248-50.*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6.*
Laporte M.M. et al. Promoter strength and tissue specificity effects on growth of tomato plants transformed with maize sucrose-phosphate synthase. Planta. Apr. 2001;212(5-6):817-22.*
Dehesh K. et al. Overexpression of 3-ketoacyl-acyl-carrier protein synthase IIIs in plants reduces the rate of lipid synthesis. Plant Physiol. Feb. 2001;125(2):1103-14.*
Hill M.A. et al. Functional analysis of conserved histidines in ADP-glucose pyrophosphorylase from *Escherichia coli*. Biochem Biophys Res Commun. Mar. 17, 1998;244(2):573-7.*
Nakanishi et al. Mutagenic analysis of functional residues in putative substrate-binding site and acidic domains of vacuolar H+-pyrophosphatase. J Biol Chem. Mar. 9, 2001;276(10):7654-60. Epub Dec. 11, 2000.*
NCBI Accession No. AAA34632 (Aug. 11, 2008) (2 pages).
NCBI Accession No. AAB64488 (Oct. 17, 2008) (2 pages).
NCBI Accession No. AAS52641 (Jun. 29, 2010) (2 pages).
NCBI Accession No. CAB91480 (Oct. 23, 2008) (2 pages).
NCBI Accession No. CAG62470 (Dec. 16, 2008) (2 pages).
NCBI Accession No. CAH03074 (Sep. 10, 2008) (2 pages).
NCBI Accession No. CAQ43469 (Apr. 29, 2008) (2 pages).
NCBI Accession No. CAR30594 (Oct. 8, 2009) (2 pages).
NCBI Accession No. CAR30849 (Jan. 14, 2010) (2 pages).
NCBI Accession No. CAY79155 (Mar. 8, 2010) (2 pages).
NCBI Accession No. DAA07642 (May 27, 2010) (2 pages).
NCBI Accession No. EDN62958 (Jul. 13, 2007) (1 page).
NCBI Accession No. EDV08821 (Jun. 16, 2008) (2 pages).
NCBI Accession No. EDZ72669 (Sep. 30, 2008) (2 pages).
NCBI Accession No. EEU04641 (Aug. 20, 2009) (2 pages).
NCBI Accession No. NP_010905 (Jun. 3, 2010) (2 pages).
NCBI Accession No. NP_984817 (Aug. 5, 2010) (2 pages).
NCBI Accession No. P32775 (Oct. 5, 2010) (4 pages).
NCBI Accession No. Q6CX53 (Aug. 10, 2010) (3 pages).
NCBI Accession No. Q6FJVO (Aug. 10, 2010) (3 pages).
NCBI Accession No. Q757Q6 (Aug. 10, 2010) (3 pages).
NCBI Accession No. Q9P5P3 (Oct. 31, 2006) (1 page).
NCBI Accession No. XP_002499104 (Jul. 22, 2009) (2 pages).
NCBI Accession No. XP_002556456 (Aug. 11, 2009) (2 pages).
NCBI Accession No. XP_449494 (Aug. 6, 2010) (2 pages).
NCBI Accession No. XP_451486 (Aug. 5, 2010) (2 pages).
NCBI Accession No. XP_963252 (Apr. 10, 2008) (2 pages).

* cited by examiner

*Primary Examiner* — Cynthia Collins
(74) *Attorney, Agent, or Firm* — Lawrence M. Lavin, Jr.; David R. Marsh; Arnold & Porter LLP

(57) ABSTRACT

Recombinant constructs and methods useful for improvement of plants are provided. In particular, recombinant constructs comprising promoters functional in plant cells positioned for expression of polynucleotides encoding starch branching enzymes from microbial sources are provided. The disclosed constructs and methods find use in production of transgenic plants to provide plants, particularly crop plants, having improved yield.

15 Claims, No Drawings

POLYNUCLEOTIDES FOR EXPRESSION OF MICROBIAL STARCH BRANCHING ENZYMES IN PLANTS FOR PRODUCTION OF PLANTS WITH IMPROVED YIELD

CROSS-REFERENCE TO RELATED APPLICATIONS

This application is a continuation of and claims priority to Ser. No. 10/369,493, filed Feb. 20, 2003 (pending with allowed claims) which claims priority under 35 U.S.C. §119 (e) of U.S. Provisional Application No. 60/360,039 filed Feb. 21, 2002, the disclosures of which applications are incorporated herein by reference in their entirety.

INCORPORATION OF SEQUENCE LISTING

Two copies of the sequence listing (Copy 1 and Copy 2) on CD-ROMs, each containing the file named pa__00433.rpt, which is 136,695,099 bytes (measured in MS-WINDOWS) and was created on Feb. 7, 2003, are herein incorporated by reference. The compliant computer readable copy of the sequence listing already on file in Ser. No. 10/369,493 is identical to the sequence listing in this application and should be used in this application.

INCORPORATION OF TABLES

Tables 1 through 21 referenced below in the detailed description are found in parent application Ser. No. 10/369,483 and are incorporated herein by reference.

FIELD OF THE INVENTION

Disclosed herein are inventions in the field of plant biochemistry and genetics. More specifically methods of producing transgenic plants having improved properties as the result of expression of microbial polypeptides are provided.

SUMMARY OF THE INVENTION

This invention provides recombinant DNA constructs which provide for expression in plant cells of polypeptides encoded by microbial genes. Expression of such polypeptides in transgenic plants leads to plants having improves phenotypic properties and/or improved response to stressful environmental conditions. Of particular interest are recombinant DNA constructs, wherein said constructs comprise a promoter functional in a plant cell, wherein said promoter is positioned to provide for expression of a polynucleotide encoding a polypeptide from a microbial source, wherein said polynucleotide is selected from the group consisting of:
  (a) a polynucleotide comprising a nucleic acid sequence selected from the group consisting of SEQ ID NO: 23688 through SEQ ID NO: 47374;
  (b) a polynucleotide encoding a polypeptide having an amino acid sequence selected from the group consisting of SEQ ID NO: 1 through SEQ ID NO: 23687;
  (c) a polynucleotide having at least 70% sequence identity to a polynucleotide of (a) or (b); and
  (d) a polynucleotide encoding a polypeptide having at least 80% sequence identity to a polypeptide having an amino acid sequence selected from the group consisting of SEQ ID NO: 1 through SEQ ID NO: 23687, wherein said encoded polypeptide is a functional homolog of said polypeptide having an amino acid sequence selected from the group consisting of SEQ ID NO: 1 through SEQ ID NO: 23687.

Such constructs are useful for production of transgenic plants having at least one improved biological property as the result of expression of a polypeptide using a construct of this invention. Improved properties of interest include yield, disease resistance, growth rate, stress tolerance and others as set forth in more detail herein.

The present invention also provides a method of improving a biological property of a plant by inserting into cells of said plant a recombinant DNA construct of the present invention.

This invention also provides transformed plants, preferably transformed crop plants, comprising a recombinant DNA construct of the present invention, and having an improved biological property as the result of the expression of a microbial polypeptide from said recombinant DNA construct.

DETAILED DESCRIPTION OF THE INVENTION

The present invention provides recombinant DNA constructs, wherein said constructs comprise a promoter functional in a plant cell, positioned to provide for expression of a polynucleotide encoding a polypeptide from a microbial source. Microbial polypeptides of interest for expression from such constructs are provided herein and are selected for their ability to impart improved properties to transformed plants as the result of modification of any one or more of a variety of plant phenotypes.

The constructs of the present invention find use in generation of transgenic plants to provide for expression of polypeptides encoded by polynucleotides, including the native microbial polynucleotides described herein. As a result of such biotechnological applications, plants, particularly crop plants, having improved properties are obtained. Crop plants of interest in the present invention include, but are not limited to soy, cotton, canola, maize, wheat, sunflower, sorghum, alfalfa, barley, millet, rice, tobacco, fruit and vegetable crops, and turf grass. Of particular interest are expression of the disclosed polypeptides to provide plants having improved yield resulting from improved utilization of key biochemical compounds, such as nitrogen, phosphorous or carbohydrate, or resulting from improved responses to environmental stresses, such as cold, heat, drought or salt, or improved response to attack by pests or pathogens. Constructs of the present invention may also be used to provide plants having improved growth and development, and ultimately increased yield, as the result of modified expression of growth regulators or modification of cell cycle or photosynthesis pathways. Other traits of interest that may be modified in plants using constructs of the present invention include seed oil and protein quantity and quality, herbicide tolerance and rate of homologous recombination.

The polynucleotides or polypeptides from a microbial source as used in this invention may be isolated from the source organism or may be obtained in some other manner, for example by de novo synthesis of polynucleotides. Thus, as used herein, the term "microbial source" indicates that the molecule was identified as naturally existing in a microbe, but does not necessarily indicate the molecule itself was specifically isolated from the source organism.

As used herein a "transgenic" organism is one whose genome has been altered by the incorporation of foreign genetic material or additional copies of native genetic material, e.g. by transformation or recombination.

It is understood that the molecules of the invention may be labeled with reagents that facilitate detection of the molecule.

As used herein, a label can be any reagent that facilitates detection, including fluorescent labels (Prober, et al, *Science* 238:336-340 (1987); Albarella et al., EP 144914), chemical labels (Sheldon et al., U.S. Pat. No. 4,582,789; Albarella et al., U.S. Pat. No. 4,563,417), or modified bases (Miyoshi et al., EP 119448), including nucleotides with radioactive elements, e.g. $^{32}P$, $^{33}P$, $^{35}S$ or $^{125}I$ such as $^{32}P$ deoxycytidine-5'-triphosphate ($^{32}PdCTP$).

Polynucleotides are capable of specifically hybridizing to other polynucleotides under certain circumstances. As used herein, two polynucleotides are said to be capable of specifically hybridizing to one another if the two molecules are capable of forming an anti-parallel, double-stranded nucleic acid structure. A nucleic acid molecule is said to be the "complement" of another nucleic acid molecule if the molecules exhibit complete complementarity. As used herein, molecules are said to exhibit "complete complementarity" when every nucleotide in each of the molecules is complementary to the corresponding nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., *Molecular Cloning*, A Laboratory Manual, 2nd Ed., Cold Spring Harbor Press, Cold Spring Harbor, N.Y. (1989), and by Haynes et al., *Nucleic Acid Hybridization, A Practical Approach*, IRL Press, Washington, D.C. (1985).

Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0×SSC at 50° C. Such conditions are known to those skilled in the art and can be found, for example in *Current Protocols in Molecular Biology*, John Wiley & Sons, N.Y. (1989), 6.3.1-6.3.6. Salt concentration and temperature in the wash step can be adjusted to alter hybridization stringency. For example, conditions may vary from low stringency of about 2.0×SSC at 40° C. to moderately stringent conditions of about 2.0×SSC at 50° C. to high stringency conditions of about 0.2×SSC at 50° C.

As used herein "sequence identity" refers to the extent to which two optimally aligned polynucleotide or peptide sequences are invariant throughout a window of alignment of components, e.g. nucleotides or amino acids. An "identity fraction" for aligned segments of a test sequence and a reference sequence is the number of identical components which are shared by the two aligned sequences divided by the total number of components in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as those in the BLAST suite of sequence analysis programs.

Polynucleotides—This invention utilizes polynucleotides that encode polypeptides identified from a microbial source. The encoded polypeptides may be the complete protein encoded by an identified microbial gene, or may be fragments of the encoded protein. Preferably, polynucleotides utilized herein encode polypeptides constituting a substantial portion of the complete protein, and more preferentially, constituting a sufficient portion of the complete protein to provide the relevant biological activity.

Of particular interest are polynucleotides that encode polypeptides involved in one or more important biological functions that are common between microbes and plants. Such polynucleotides may be expressed in transgenic plants to produce plants having improved phenotypic properties and/or improved response to stressful environmental conditions. See, for example, Tables 3-21 for a list of improved plant properties and responses and the SEQ ID NOs representing exemplary polynucleotides that may be expressed in transgenic plants to impart such improvements.

Polynucleotides of the present invention are generally used to impart such biological properties by providing for enhanced protein activity in a transgenic organism, preferably a transgenic plant. Enhanced protein activity is evaluated by reference to a wild type cell or organism and can be determined by direct or indirect measurement. Direct measurement of protein activity might include an analytical assay for the protein, per se, or enzymatic product of protein activity. Indirect assay might include measurement of a property affected by the protein.

The polynucleotides that find use in this invention represent genes from a variety of bacterial and fungal sources as shown in Table 1. Nucleic acid sequences of polynucleotides for use in the constructs of the present invention are exemplified herein by the native microbial polynucleotide sequences provided as SEQ ID NO: 23688 through SEQ ID NO: 47374.

Also of interest for use in the constructs of the present invention are variants of the polynucleotides provided herein. Such variants may be naturally occurring, including homologous polynucleotides from the same or a different species, or may be non-natural variants, for example polynucleotides synthesized using chemical synthesis methods, or generated using recombinant DNA techniques. Degeneracy of the genetic code provides the possibility to substitute at least one base of the protein encoding sequence of a gene with a different base without causing the amino acid sequence of the polypeptide produced from the gene to be changed. Hence, the DNA utilized in the present invention may also have any base sequence that has been changed from SEQ ID NO: 23688 through SEQ ID NO: 47374 by substitution in accordance with degeneracy of the genetic code.

Also of interest regarding variant sequences for expression of microbial polypeptides in plants is the use of polynucleotides optimized for efficient expression of the encoded polypeptide in plants. For example, the encoding polynucleotides can be synthesized or modified using plant preferred codons for improved expression. It is recognized that all or any part of the encoding sequence may be optimized by synthesis or modification, and that partially optimized polynucleotides are also of interest for expression of microbial polypeptides for modification of plant properties. Codon usage tables may be used to identify plant preferred codons, for example by identifying the codons of highest frequency in the proteins expressed in the largest amount in the particular plant species of interest, and to avoid the use of codons that are rarely found in plants. References describing codon usage include: U.S. Pat. No. 5,500,365, Nakamura et al. (2000) *Nucl. Acids Res.* 28:292, Perlak et al. (1991) *Proc. Natl. Acad.*

*Sci. USA* 88:3324-3328, Carels et al. (1998) *J Mol. Evol.* 46: 45 and Fennoy et al. (1993) *Nucl. Acids Res.* 21(23):5294. Codon usage tables for a number of plant species are also available from the Department of Plant Gene Research at the Kazusa DNA Research Institute, Japan, for example at www.kazusa.or.jp/codon/.

Additional sequence modifications are known to enhance gene expression in plant hosts. These include elimination of sequences encoding spurious polyadenylation signals, exon-intron splice site signals, transposon-like repeats, hairpin secondary mRNA structures and other such well-characterized sequences which may be deleterious to gene expression. The G-C content of the sequence may also be adjusted to levels generally used by the target plant host. For example, some microbial genes are very rich (>60%) in adenine (A) and thymine (T) while plant genes are on the order of 45-55% A+T. It is also preferred that regions comprising many consecutive A+T bases or G+C bases are disrupted since these regions are predicted to have a higher likelihood to form hairpin structure due to self-complementarity. Therefore, insertion of heterogeneous base pairs would reduce the likelihood of self-complementary secondary structure formation which are known to inhibit transcription and/or translation in some organisms. In most cases, the adverse effects may be minimized by using sequences which do not contain more than five consecutive A+T or G+C.

As discussed above, modification of the DNA sequences of wild-type genes and construction of t a completely synthetic gene for a given amino acid sequence are both desirable methods for increasing the expression level of non-plant genes in plant cells. In general, regions with multiple consecutive A+T or G+C nucleotides should be avoided. Codons should be selected avoiding the TA and CG doublets where possible. Codon usage can be normalized against a plant preferred codon usage table and the G+C content preferably adjusted to about 50%. The resulting sequence should also be examined to ensure that there are minimal putative plant polyadenylation signals and ATTTA sequences.

Polynucleotides for use in constructs of the present invention that are variants of the polynucleotides described herein will generally demonstrate significant identity with the polynucleotides provided herein. Of particular interest are polynucleotide homologs having at least about 60% sequence identity, at least about 70% sequence identity, at least about 80% sequence identity, at least about 85% sequence identity, and more preferably at least about 90%, 95% or even greater, such as 98% or 99% sequence identity with polynucleotide sequences described herein.

Protein and Polypeptide Molecules—This invention encompasses recombinant DNA expression constructs that provide for production of polypeptides from microbial sources in plants and/or plant cells. Amino acid sequences of the polypeptides of interest for expression using constructs of the present invention are provided herein as SEQ ID NO: 1 through SEQ ID NO: 23687.

As used herein, the term "polypeptide" means an unbranched chain of amino acid residues that are covalently linked by an amide linkage between the carboxyl group of one amino acid and the amino group of another. The term polypeptide can encompass whole proteins (i.e. a functional protein encoded by a particular gene), as well as fragments of proteins. Of particular interest are polypeptides which represent whole proteins or a sufficient portion of the entire protein to impart the relevant biological activity of the protein. The term "protein" also includes molecules consisting of one or more polypeptide chains. Thus, a polypeptide for use in constructs of the present invention may also constitute an entire gene product, but only a portion of a functional oligomeric protein having multiple polypeptide chains.

Of particular interest for expression from constructs of the present invention are polypeptides involved in one or more important biological properties in plants. Such polypeptides may be produced in transgenic plants to provide plants having improved phenotypic properties and/or improved response to stressful environmental conditions. See, Tables 3-21 for improved plant properties and responses and the SEQ ID NOs for the polypeptides whose expression in transgenic plants is of interest to impart such improvements. A summary of such improved properties and polypeptides of interest is provided below.

Yield/Nitrogen: Yield improvement by improved nitrogen flow, sensing, uptake, storage and/or transport. Polypeptides useful for imparting such properties include those involved in aspartate and glutamate biosynthesis, polypeptides involved in aspartate and glutamate transport, polypeptides associated with the TOR (Target of Rapamycin) pathway, nitrate transporters, ammonium transporters, chlorate transporters and polypeptides involved in tetrapyrrole biosynthesis.

Yield/Carbohydrate: Yield improvement by effects on carbohydrate metabolism, for example by increased sucrose production and/or transport. Polypeptides useful for improved yield by effects on carbohydrate metabolism include polypeptides involved in sucrose or starch metabolism, carbon assimilation or carbohydrate transport, including, for example sucrose transporters or glucose/hexose transporters, enzymes involved in glycolysis/gluconeogenesis, the pentose phosphate cycle, or raffinose biosynthesis, and polypeptides involved in glucose signaling, such as SNF1 complex proteins.

Yield/Photosynthesis: Yield improvement resulting from increased photosynthesis. Polypeptides useful for increasing the rate of photosynthesis include phytochrome, photosystem I and II proteins, electron carriers, ATP synthase, NADH dehydrogenase and cytochrome oxidase.

Yield/Phosphorus: Yield improvement resulting from increased phosphorus uptake, transport or utilization. Polypeptides useful for improving yield in this manner include phosphatases and phosphate transporters.

Yield/Stress tolerance: Yield improvement resulting from improved plant growth and development by helping plants to tolerate stressful growth conditions. Polypeptides useful for improved stress tolerance under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and homoglobin. Enhanced activity of such polypeptides in transgenic plants will provide changes in the ability of a plant to respond to a variety of environmental stresses, such as chemical stress, drought stress and pest stress.

Cold tolerance: Polypeptides of interest for improving plant tolerance to cold or freezing temperatures include polypeptides involved in biosynthesis of trehalose or raffinose, polypeptides encoded by cold induced genes, fatty acyl desaturases and other polypeptides involved in glycerolipid or membrane lipid biosynthesis, which find use in modification of membrane fatty acid composition, alternative oxidase, calcium-dependent protein kinases, LEA proteins and uncoupling protein.

Heat tolerance: Polypeptides of interest for improving plant tolerance to heat include polypeptides involved in biosynthesis of trehalose, polypeptides involved in glycerolipid biosynthesis or membrane lipid metabolism (for altering membrane fatty acid composition), heat shock proteins and mitochondrial NDK.

Osmotic tolerance: Polypeptides of interest for improving plant tolerance to extreme osmotic conditions include polypeptides involved in proline biosynthesis.

Drought tolerance: Polypeptides of interest for improving plant tolerance to drought conditions include aquaporins, polypeptides involved in biosynthesis of trehalose or wax, LEA proteins and invertase.

Pathogen or pest tolerance: Polypeptides of interest for improving plant tolerance to effects of plant pests or pathogens include proteases, polypeptides involved in anthocyanin biosynthesis, polypeptides involved in cell wall metabolism, including cellulases, glucosidases, pectin methylesterase, pectinase, polygalacturonase, chitinase, chitosanase, and cellulose synthase, and polypeptides involved in biosynthesis of terpenoids or indole for production of bioactive metabolites to provide defense against herbivorous insects.

Cell cycle modification: Polypeptides encoding cell cycle enzymes and regulators of the cell cycle pathway are useful for manipulating growth rate in plants to provide early vigor and accelerated maturation leading to improved yield. Improvements in quality traits, such as seed oil content, may also be obtained by expression of cell cycle enzymes and cell cycle regulators. Polypeptides of interest for modification of cell cycle pathway include cyclins and EIF5alpha pathway proteins, polypeptides involved in polyamine metabolism, polypeptides which act as regulators of the cell cycle pathway, including cyclin-dependent kinases (CDKs), CDK-activating kinases, CDK-inhibitors, Rb and Rb-binding proteins, and transcription factors that activate genes involved in cell proliferation and division, such as the E2F family of transcription factors, proteins involved in degradation of cyclins, such as cullins, and plant homologs of tumor suppressor polypeptides.

Seed protein yield/content: Polypeptides useful for providing increased seed protein quantity and/or quality include polypeptides involved in the metabolism of amino acids in plants, particularly polypeptides involved in biosynthesis of methionine/cysteine and lysine, amino acid transporters, amino acid efflux carriers, seed storage proteins, proteases, and polypeptides involved in phytic acid metabolism.

Seed oil yield/content: Polypeptides useful for providing increased seed oil quantity and/or quality include polypeptides involved in fatty acid and glycerolipid biosynthesis, beta-oxidation enzymes, enzymes involved in biosynthesis of nutritional compounds, such as carotenoids and tocopherols, and polypeptides that increase embryo size or number or thickness of aleurone.

Disease response in plants: Polypeptides useful for imparting improved disease responses to plants include polypeptides encoded by cercosporin induced genes, antifungal proteins and proteins encoded by R-genes or SAR genes. Expression of such polypeptides in transgenic plants will provide an increase in disease resistance ability of plants.

Galactomannanan biosynthesis: Polypeptides involved in production of galactomannans are of interest for providing plants having increased and/or modified reserve polysaccharides for use in food, pharmaceutical, cosmetic, paper and paint industries.

Flavonoid/isoflavonoid metabolism in plants: Polypeptides of interest for modification of flavonoid/isoflavonoid metabolism in plants include cinnamate-4-hydroxylase, chalcone synthase and flavonol synthase. Enhanced activity of such polypeptides in transgenic plants will provide changes in the quantity and/or speed of flavonoid metabolism in plants and may improve disease resistance by enhancing synthesis of protective secondary metabolites or improving signaling pathways governing disease resistance.

Growth regulators: Polypeptides involved in production of substances that regulate the growth of various plant tissues are of interest in the present invention and may be used to provide transgenic plants having altered morphologies and improved plant growth and development profiles leading to improvements in yield and stress response. Of particular interest are polypeptides involved in the biosynthesis of plant growth hormones, such as gibberellins, cytokinins, auxins, ethylene and abscisic acid, and other proteins involved in the activity and/or transport of such polypeptides, including for example, cytokinin oxidase, cytokinin/purine permeases, F-box proteins, G-proteins and phytosulfokines.

Herbicide tolerance: Polypeptides of interest for producing plants having tolerance to plant herbicides include polypeptides involved in the shikimate pathway, which are of interest for providing glyphosate tolerant plants. Such polypeptides include polypeptides involved in biosynthesis of chorismate, phenylalanine, tyrosine and tryptophan.

Homologous recombination: Increasing the rate of homologous recombination in plants is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, including for example, resolvases and polypeptide members of the RAD52 epistasis group.

Lignin biosynthesis: Polypeptides involved in lignin biosynthesis are of interest for increasing plants' resistance to lodging and for increasing the usefulness of plant materials as biofuels.

The function of polypeptides used in constructs of the present invention may be known from previous experimental evidence, or may be determined by comparison of the amino acid sequence of the polypeptides to amino acid sequences of other polypeptides for which a function is known. A variety of homology based search algorithms are available to compare a query sequence to a protein database, including for example, BLAST, FASTA, and Smith-Waterman. In the present application, BLASTX and BLASTP algorithms are used to provide protein function information. A number of values are examined in order to assess the confidence of the function assignment. Useful measurements include "E-value" (also shown as "hit_p"), "percent identity", "percent query coverage", and "percent hit coverage".

In BLAST, E-value, or expectation value, represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GenBank, have generally increased over time for any given query/entry match. In setting criteria for confidence of polypeptide function prediction, a "high" BLAST match is considered herein as having an E-value for the top BLAST hit provided in Table 1 of less than 1E-30; a medium BLASTX E-value is 1E-30 to 1E-8; and a low BLASTX E-value is greater than 1E-8.

Percent identity refers to the percentage of identically matched amino acid residues that exist along the length of that portion of the sequences which is aligned by the BLAST algorithm. In setting criteria for confidence of polypeptide function prediction, a "high" BLAST match is considered herein as having percent identity for the top BLAST hit provided in Table 1 of at least 70%; a medium percent identity value is 35% to 70%; and a low percent identity is less than 35%.

Of particular interest in protein function assignment in the present invention is the use of combinations of E-values, percent identity, query coverage and hit coverage. Query coverage refers to the percent of the query sequence that is represented in the BLAST alignment. Hit coverage refers to the percent of the database entry that is represented in the BLAST alignment. In the present invention, function of a query polypeptide is inferred from function of a protein homolog where either (1) (hit_p<1e-30 or % identity>35%) AND query_coverage>50% AND hit_coverage>50%, or (2) hit_p<1e-8 AND query_coverage>70% AND hit_coverage>70%.

Functional homologs which differ in one or more amino acids from those of a polypeptide described herein as the result of one or more conservative amino acid substitutions are also of interest for expression in plants using the constructs of the present invention. It is well known in the art that one or more amino acids in a native sequence can be substituted with at least one other amino acid, the charge and polarity of which are similar to that of the native amino acid, resulting in a silent change. For instance, valine is a conservative substitute for alanine and threonine is a conservative substitute for serine. Conservative substitutions for an amino acid within the native polypeptide sequence can be selected from other members of the class to which the naturally occurring amino acid belongs. Amino acids can be divided into the following four groups: (1) acidic amino acids, (2) basic amino acids, (3) neutral polar amino acids, and (4) neutral nonpolar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. Also of interest for expression in transgenic plants using constructs as described herein are polypeptides which differ in one or more amino acids from those of a microbial polypeptide described herein as the result of deletion or insertion of one or more amino acids in a native sequence.

Also of interest for use in constructs of the present invention are functional homologs of the polypeptides described herein which have the same function as a microbial polypeptide provided herein, but with increased or decreased activity or altered specificity. Such variations in protein activity may exist naturally in polypeptides encoded by related genes, for example in a related polypeptide encoded by a different allele or in a different species, or can be achieved by mutagenesis. Naturally occurring variant polypeptides may be obtained by well known nucleic acid or protein screening methods using DNA or antibody probes, for example by screening libraries for genes encoding related polypeptides, or in the case of expression libraries, by screening directly for variant polypeptides. Screening methods for obtaining a modified protein or enzymatic activity of interest by mutagenesis are disclosed in U.S. Pat. No. 5,939,250. An alternative approach to the generation of variants uses random recombination techniques such as "DNA shuffling" as disclosed in U.S. Pat. Nos. 5,605,793; 5,811,238; 5,830,721 and 5,837,458; and International Applications WO 98/31837 and WO 99/65927, all of which are incorporated herein by reference. An alternative method of molecular evolution involves a staggered extension process (StEP) for in vitro mutagenesis and recombination of nucleic acid molecule sequences, as disclosed in U.S. Pat. No. 5,965,408 and International Application WO 98/42832, both of which are incorporated herein by reference.

Polypeptide variants useful for expression in transgenic plants will generally demonstrate significant identity with the polypeptides described herein. Of particular interest are polypeptides having at least about 35% sequence identity, at least about 50% sequence identity, at least about 60% sequence identity, at least about 70% sequence identity, at least about 80% sequence identity, and more preferably at least about 85%, 90%, 95% or even greater, sequence identity with polypeptide sequences described herein. Of particular interest in the present invention are polypeptides having amino acid sequences provided herein (reference polypeptides) and functional homologs of such reference polypeptides, wherein such functional homologs comprises at least 50 consecutive amino acids having at least 80% identity to a 50 amino acid polypeptide fragment of said reference polypeptide.

Recombinant DNA Constructs—The present invention encompasses the use of polynucleotides described herein in recombinant constructs, i.e. constructs comprising polynucleotides that are constructed or modified outside of cells and that join nucleic acids that are not found joined in nature. Using methods known to those of ordinary skill in the art, polypeptide encoding sequences of this invention can be inserted into recombinant DNA constructs that can be introduced into a host cell of choice for expression of the encoded protein. Of particular interest in the present invention is the use of the polynucleotides of the present invention for preparation of constructs for use in plant transformation.

In plant transformation, exogenous genetic material is transferred into a plant cell. By "exogenous" it is meant that a nucleic acid molecule, for example a recombinant DNA construct comprising a polynucleotide of the present invention, is produced outside the organism, e.g. plant, into which it is introduced. An exogenous nucleic acid molecule can have a naturally occurring or non-naturally occurring nucleotide sequence. One skilled in the art recognizes that an exogenous nucleic acid molecule can be derived from the same species into which it is introduced or from a different species. Such exogenous genetic material may be transferred into either monocot or dicot plants including, but not limited to, soy, cotton, canola, maize, teosinte, wheat, rice and *Arabidopsis* plants. Transformed plant cells comprising such exogenous genetic material may be regenerated to produce whole transformed plants.

Exogenous genetic material may be transferred into a plant cell by the use of a DNA vector or construct designed for such a purpose. A construct can comprise a number of sequence elements, including promoters, encoding regions, and selectable markers. Vectors are available which have been designed to replicate in both *E. coli* and *A. tumefaciens* and have all of the features required for transferring large inserts of DNA into plant chromosomes. Design of such vectors is generally within the skill of the art. See, for example, *Plant Molecular Biology: A Laboratory Manual*, Clark (ed.), Springier, N.Y. (1997).

A construct will generally include a plant promoter to direct transcription of the protein encoding region of choice. Numerous promoters that are active in plant cells have been described in the literature. These include the nopaline synthase (NOS) promoter and octopine synthase (OCS) promoters carried on tumor-inducing plasmids of *Agrobacterium tumefaciens*, caulimovirus promoters such as the cauliflower mosaic virus (CaMV) 19S promoter (Lawton et al., *Plant Mol. Biol.* 9:315-324 (1987) and $^{35}$S promoter (Odell et al., *Nature* 313:810-812 (1985), CaMV enhanced 35S promoter and the figwort mosaic virus 35S-promoter. Other desirable promoters include the light-inducible promoter from the small subunit of ribulose-1,5-bis-phosphate carboxylase (ss-RUBISCO), the actin 1 promoter from rice (McElroy et al (1991) *Mol. Gen. Genet.* 231:150-160) or maize (Wang et al (1992) *Molecular and Cellular Biology* 12:3399-3406), the Adh promoter (Walker et al., *Proc. Nat. Acad. Sci.* (U.S.A.) 84:6624-6628 (1987), the sucrose synthase promoter (Yang et al. (1990) *Proc. Natl. Acad. Sci.* (U.S.A.) 87:4144-4148), the R gene complex promoter (Chandler et al. (1989) *The Plant Cell* 1:1175-1183), and the chlorophyll a/b binding protein gene promoter. These promoters and numerous others have been used to create DNA constructs for expression in plants. See, for example, PCT publication WO 84/02913. Any promoter known or found to cause transcription of DNA in plant cells can be used in the invention. Other useful promoters are described, for example, in U.S. Pat. Nos. 5,378,619; 5,391,725; 5,428,147; 5,447,858; 5,608,144; 5,608,144; 5,614,399; 5,633,441; 5,633,435; and 4,633,436, all of which are incorporated herein by reference.

In addition, promoter enhancers, such as the CaMV 35S enhancer (Kay et al. (1987) *Science* 236:1299-1302) or a tissue specific enhancer (Fromm et al. (1989) *The Plant Cell* 1:977-984), may be used to enhance gene transcription levels. Enhancers often are found 5' to the start of transcription in a promoter that functions in eukaryotic cells, but can often be inserted in the forward or reverse orientation 5' or 3' to the coding sequence. In some instances, these 5' enhancing elements are introns. Deemed to be particularly useful as enhancers are the 5' introns of the rice actin 1 and rice actin 2 genes. Examples of other enhancers which can be used in accordance with the invention include elements from octopine synthase genes (Ellis et al. (1987) *EMBO Journal* 6:3203-3208), the maize alcohol dehydrogenase gene intron 1 (Callis et al. (1987) *Genes and Develop.* 1:1183-1200), elements from the maize shrunken 1 gene, the sucrose synthase intron (Vasil et al. (1989) *Plant Physiol.* 91:1575-1579) and the TMV omega element (Gallie et al. (1989) *The Plant Cell* 1:301-311), and promoters from non-plant eukaryotes (e.g., yeast; Ruden et al. (1988) *Proc Natl. Acad. Sci.* 85:4262-4266). DNA constructs can also contain one or more 5' non-translated leader sequences which serve to enhance polypeptide production from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al. (1996) *Plant Mol. Biol.* 32:393-405).

Constructs and vectors may also include, with the coding region of interest, a nucleic acid sequence that acts, in whole or in part, to terminate transcription of that region. One type of 3' untranslated sequence which may be used is a 3' UTR from the nopaline synthase gene (nos 3') of *Agrobacterium tumefaciens* (Bevan et al. (1983) *Nucleic Acids Res.* 11:369-385). Other 3' termination regions of interest include those from a gene encoding the small subunit of a ribulose-1,5-bisphosphate carboxylase-oxygenase (rbcS), and more specifically, from a rice rbcS gene (PCT Publication WO 00/70066), the 3' UTR for the T7 transcript of *Agrobacterium tumefaciens* (Dhaese et al. (1983) *EMBO J* 2:419-426), the 3' end of the protease inhibitor I or II genes from potato (An et al. (1989) *Plant Cell* 1:115-122) or tomato (Pearce et al. (1991) *Science* 253:895-898), and the 3' region isolated from Cauliflower Mosaic Virus (Timmermans et al. (1990) *J Biotechnol* 14:333-344). Alternatively, one also can use a gamma coixin, oleosin 3 or other 3' UTRs from the genus *Coix* (PCT Publication WO 99/58659).

Constructs and vectors may also include a selectable marker. Selectable markers may be used to select for plants or plant cells that contain the exogenous genetic material. Examples of such include, but are not limited to, a nptII gene (Potrykus et al. (1985) *Mol. Gen. Genet.* 199:183-188) which codes for kanamycin resistance and can be selected for using kanamycin, G418, etc.; a bar gene which codes for bialaphos resistance; a mutant EPSP synthase gene (Hinchee et al. (1988) *Bio/Technology* 6:915-922) which encodes glyphosate resistance; a nitrilase gene which confers resistance to bromoxynil (Stalker et al. (1988) *J. Biol. Chem.* 263:6310-6314); a mutant acetolactate synthase gene (ALS) which confers imidazolinone or sulphonylurea resistance (European Patent Application 154,204 (Sep. 11, 1985)); and a methotrexate resistant DHFR gene (Thillet et al. (1988) *J. Biol. Chem.* 263:12500-12508.

Constructs and vectors may also include a screenable marker. Screenable markers may be used to monitor transformation. Exemplary screenable markers include a β-glucuronidase or uidA gene (GUS) which encodes an enzyme for which various chromogenic substrates are known (Jefferson (1987) *Plant Mol. Biol, Rep.* 5.387-405); Jefferson et al. (1987) *EMBO J.* 6.3901-3907); an R-locus gene, which encodes a product that regulates the production of anthocyanin pigments (red color) in plant tissues (Dellaporta et al. (1988) Stadler Symposium 11:263-282); Other possible selectable and/or screenable marker genes will be apparent to those of skill in the art.

Constructs and vectors may also include a transit peptide for targeting of a gene target to a plant organelle, particularly to a chloroplast, leucoplast or other plastid organelle (European Patent Application Publication Number 0218571).

For use in *Agrobacterium* mediated transformation methods, constructs of the present invention will also include T-DNA border regions flanking the DNA to be inserted into the plant genome to provide for transfer of the DNA into the plant host chromosome as discussed in more detail below. An exemplary plasmid that finds use in such transformation methods is pCGN8640, a T-DNA vector that can be used to clone exogenous genes and transfer them into plants using *Agrobacterium*-mediated transformation. pCGN8640 has the restriction sites BamH1, NotI, HindIII, PstI, and SacI positioned between a $^{35}$S promoter element and a transcription terminator. Flanking this DNA are the left border and right border sequences necessary for *Agrobacterium* transformation. The plasmid also has origins of replication for maintaining the plasmid in both *E. Coli* and *Agrobacterium tumefaciens* strains. A spectinomycin resistance gene on the plasmid can be used to select for the presence of the plasmid in both *E. coli* and *Agrobacterium tumefaciens*.

A candidate gene is prepared for insertion into the T-DNA vector, for example using well-known gene cloning techniques such as PCR. Restriction sites may be introduced onto each end of the gene to facilitate cloning. For example, candidate genes may be amplified by PCR techniques using a set of primers. Both the amplified DNA and the cloning vector are cut with the same restriction enzymes, for example, NotI and PstI. The resulting fragments are gel-purified, ligated together, and transformed into *E. coli*. Plasmid DNA containing the vector with inserted gene may be isolated from *E. coli* cells selected for spectinomycin resistance, and the presence to the desired insert in pCGN8640 verified by digestion with the appropriate restriction enzymes. Undigested plasmid may then be transformed into *Agrobacterium tumefaciens* using techniques well known to those in the art, and transformed *Agrobacterium* cells containing the vector of interest selected based on spectinomycin resistance. These and other similar constructs useful for plant transformation may be readily prepared by one skilled in the art.

Transformation Methods and Transgenic Plants—Methods and compositions for transforming bacteria and other microorganisms are known in the art. See for example Sambrook et al. (1989) *Molecular Cloning: A Laboratory Manual*, Second Edition, Cold Spring Harbor Laboratory Press, Cold Spring Harbor, N.Y.).

Technology for introduction of DNA into cells is well known to those of skill in the art. Known methods for delivering a gene into cells include: (a) chemical methods (Graham and van der Eb (1973) *Virology* 54:536-539); (b) physical methods such as microinjection (Capecchi (1980) *Cell* 22:479-488), electroporation (Wong and Neumann (1982) *Biochem. Biophys. Res. Commun.* 107:584-587); Fromm et al. (1985) *Proc. Natl. Acad. Sci.* (U.S.A.) 82:5824-5828); U.S. Pat. No. 5,384,253); the gene gun (Johnston and Tang (1994) *Methods Cell Biol.* 43:353-365); (c) viral vectors (Clapp (1993) *Clin. Perinatol.* 20:155-168); Lu et al. (1993) *J. Exp. Med.* 178:2089-2096); Eglitis and Anderson (1988) *Biotechniques* 6:608-614); (d) receptor-mediated mechanisms (Curiel et al. (1992) *Hum. Gen. Ther.* 3:147-154), Wagner et al. (1992) *Proc. Natl. Acad. Sci.* (USA) 89:6099-6103); and (e) *Agrobacterium tumefaciens*-mediated transformation of plants (Fraley et al., Bio/Technology 3:629-635 (1985); and Rogers et al. (1987) *Methods Enzymol.* 153:253-277). In addition, DNA constructs and methods for stably transforming plant plastids have been described; see, for example U.S. Pat. No. 5,877,402, incorporated herein by reference.

After transformation, the transformed plant cells or tissues may be grown in an appropriate medium to promote cell proliferation and regeneration. In the case of protoplasts the cell wall will first be allowed to reform under appropriate osmotic conditions, and the resulting callus introduced into a nutrient regeneration medium to promote the formation of shoots and roots. For gene gun transformation of wheat and maize see U.S. Pat. Nos. 6,153,812 and 6,160,208, both of which are incorporated herein by reference. See also, Chistou (1996) *Particle Bombardment for Genetic Engineering of Plants*, Biotechnology Intelligence Unit, Academic Press, San Diego, Calif.), and in particular, pp. 63-69 (maize), and pp 50-60 (rice).

The use of *Agrobacterium*-mediated plant integrating vectors to introduce DNA into plant cells for production of stably transformed whole plants is well known in the art. The region of DNA to be transferred into the host genome is defined by the tDNA border sequences in *Agrobacterium*-mediated plant integrating vectors and intervening DNA is usually inserted into the plant genome as described (Spielmann et al. (1986) *Mol. Gen. Genet.* 205:34). See also U.S. Pat. Nos. 5,416,011; 5,463,174; and 5,959,179 for *Agrobacterium* mediated transformation of soy; U.S. Pat. Nos. 5,591,616 and 5,731,179 for *Agrobacterium* mediated transformation of monocots such as maize; and U.S. Pat. No. 6,037,527 for *Agrobacterium* mediated transformation of cotton, all of which are incorporated herein by reference. Modern *Agrobacterium* transformation vectors are capable of replication in *E. coli* as well as *Agrobacterium*, allowing for convenient manipulations (Klee et al. (1985) In: Plant DNA Infectious Agents, Hohn and Schell (eds.), Springer-Verlag, New York, pp. 179-203).

Microprojectile bombardment techniques are also widely applicable, and may be used to transform virtually any plant species. Examples of species which have been transformed by microprojectile bombardment include monocot species such as maize (PCT Publication WO 95/06128), barley, wheat (U.S. Pat. No. 5,563,055), rice, oats, rye, sugarcane, and sorghum, and dicot species including tobacco, soybean (U.S. Pat. No. 5,322,783), sunflower, cotton, tomato, and legumes in general (U.S. Pat. No. 5,563,055).

Any of the constructs of the present invention may be introduced into a plant cell in a permanent or transient manner in combination with other genetic elements such as vectors, promoters enhancers etc. Further any of the constructs of the present invention may be introduced into a plant cell in a manner that allows for production in the plant cell of one or more polypeptides encoded by microbial polynucleotides in the construct.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Expression of microbial polynucleotides using constructs of the present invention and the concomitant production of polypeptides encoded by the polynucleotides is of interest for production of transgenic plants having improved properties, particularly, improved properties which result in crop plant yield improvement. Expression of polypeptides in plant cells may be evaluated by specifically identifying the protein products of the introduced genes or evaluating the phenotypic changes brought about by their expression.

Assays for the production and identification of specific proteins make use of various physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, particularly where the expressed protein is an enzyme capable of catalyzing chemical reactions involving specific substrates and products. These reactions may be measured, for example in plant extracts, by providing and quantifying the loss of substrates or the generation of products of the reactions by physical and/or chemical procedures.

In many cases, the expression of a gene product is determined by evaluating the phenotypic results of its expression. Such evaluations may be simply as visual observations, or may involve assays. Such assays may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning. A Laboratory Manual*, Cold Spring Harbor Press (1989); Mailga et al., *Methods in Plant Molecular Biology*, Cold Spring Harbor Press (1995; Birren et al., *Genome Analysis. Analyzing DNA*, 1, Cold Spring Harbor, N.Y. (1998)).

Having now generally described the invention, the same will be more readily understood through reference to the following example which is provided by way of illustration, and are not intended to be limiting of the present invention, unless specified.

EXAMPLE

Functions of polypeptides encoded by the microbial polynucleotide sequences described herein are determined using a hierarchical classification tool, termed FunCAT, for Functional Categories Annotation Tool. Most categories collected in FunCAT are classified by function, although other criteria are used, for example, cellular localization or temporal process. The assignment of a functional category to a query sequence is based on BLASTX sequence search, which compares two protein sequences. FunCAT assigns categories by iteratively scanning through all BLAST hits, starting with the most significant match, and reporting the first category assignment for each FunCAT source classification scheme. In the present invention, function of a query polypeptide is inferred from the function of a protein homolog where either (1) (hit_p<e-30 or % identity>35%) AND query_coverage>50% AND hit_coverage>50%, or (2) hit_p<1e-8 AND query_coverage>70% AND hit_coverage>70%.

Functional assignments from five public classification schemes, GO_BP, GO_CC, GO_MF, KEGG and EC, and one internal Monsanto classification scheme, POI, are provided in Table 1. The column under the heading "cat_type" indicates the source of the classification. GO_BP=Gene Ontology Consortium-biological process; GO_CC=Gene Ontology Consortium-cellular component; GO_MF=Gene Ontology Consortium-molecular function; KEGG=KEGG functional hierarchy; EC=Enzyme Classification from ENZYME data bank release 25.0; POI=Pathways of Interest. The column under the heading "cat_desc" provides the name of the subcategory into which the query sequence was classified. The column under the heading "hit_desc" provides a description of the BLAST hit to the query sequences that led to the specific classification. The column under the heading "hit_p" provides the e-value for the BLAST hit.

Table 2 provides the SEQ ID NO (SEQ NUM), sequence designation (SEQ ID) of exemplary DNA sequence encoding the polypeptides described in Table 1. Table 2 also provides the SEQ ID NO (Prot Num) and sequence designation (Prot ID) of the proteins encoded by the nucleotide sequences.

Sequences useful for producing transgenic plants having improved biological properties are identified from their FunCAT annotations and are provided in Tables 3-21.

| Table | Biological Property |
|---|---|
| 3 | Cold Tolerance |
| 4 | Disease Control |
| 5 | Drought Tolerance |
| 6 | Plant Growth/Cell Cycle |
| 7 | Plant Growth/Growth Regulators |
| 8 | Heat Tolerance |
| 9 | Herbicide Tolerance |
| 10 | Homologous Recombination |
| 11 | Osmotic Tolerance |
| 12 | Pathogen/Pest Tolerance |
| 13 | Seed Oil Yield/Content |
| 14 | Seed Protein Yield/Content |
| 15 | Yield: Carbohydrate |
| 16 | Yield: Nitrogen |
| 17 | Yield: Phosphorus |
| 18 | Yield: Photosynthesis |
| 19 | Yield: Stress Tolerance |
| 20 | Lignin Biosynthesis |
| 21 | Galactomannan Biosynthesis |

A biological property of particular interest is plant yield. Plant yield may be improved by alteration of a variety of plant pathways, including those involving nitrogen, carbohydrate, or phosphorus utilization and/or uptake. Plant yield may also be improved by alteration of a plant's photosynthetic capacity or by improving a plant's ability to tolerate a variety of environmental stresses, including cold, heat, drought and osmotic stresses. Other biological properties of interest that may be improved using sequences of the present invention include pathogen or pest tolerance, herbicide tolerance, disease resistance, growth rate (for example by modification of cell cycle or expression of growth regulators), seed oil and/or protein yield and quality, rate and control of recombination, and lignin content.

Table 1 Column Descriptions

Seq num provides the SEQ ID NO for the listed polynucleotide sequences.

SeqID provides an arbitrary sequence name taken from the name of the clone from which the cDNA sequence was obtained.

cat_type indicates the classification scheme used to classify the sequence. GO_BP=Gene Ontology Consortium-biological process; GO_CC=Gene Ontology Consortium-cellular component; GO_MF=Gene Ontology Consortium-molecular function; KEGG=KEGG functional hierarchy (KEGG=Kyoto Encyclopedia of Genes and Genomes); EC=Enzyme Classification from ENZYME data bank release 25.0; POI=Pathways of Interest.

cat_desc provides the classification scheme subcategory to which the query sequence was assigned.

hit_desc provides the description of the BLAST hit which resulted in assignment of the sequence to the function category provided in the cat_desc column.

hit_p provides the E value for the BLAST hit in the hit_desc column.

pct_ident refers to the percentage of identically matched nucleotides (or residues) that exist along the length of that portion of the sequences which is aligned in the BLAST match provided in hit_desc.

qry_range lists the range of the query sequence aligned with the hit.

hit_range lists the range of the hit sequence aligned with the query.

qry cvrg provides the percent of query sequence length that matches to the hit (NCBI) sequence in the BLAST match (% qry cvrg=(match length/query total length)×100).

hit cvrg provides the percent of hit sequence length that matches to the query sequence in the match generated using BLAST (% hit cvrg=(match length/hit total length)×100).

Species provides the name of the organism from which the cDNA was isolated.

Product_concept column provides the plant biological properties that may be modified by expression of the listed polypeptides.

1720 MRT4932__17228P POI Oil Biosynthesis\Starch Metabolism\Starch branching enzyme [GI:2117726] [DE:1,4-alpha-glucan branching enzyme (EC 2.4.1.18) isoform SBE2.1 precursor—*Arabidopsis thaliana* (fragment)] [OS: *Arabidopsis thaliana*] 0.0 52 5-701 150-831 99 80 *Saccharomyces cerevisiae*

YIELD:CARBOHYDRATE SEED_OIL_YIELD/CONTENT

All publications and patent applications cited herein are incorporated by reference in their entirely to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

---

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09024113B2). An electronic copy of the "Sequence Listing" will also be available from the USPTO upon request and payment of the fee set forth in 37 CFR 1.19(b)(3).

---

What is claimed is:

1. A recombinant DNA construct comprising a promoter functional in a plant cell, wherein said promoter is positioned to provide for expression of a polynucleotide encoding a polypeptide, and wherein said polynucleotide is selected from the group consisting of:
   (a) a polynucleotide comprising the nucleic acid sequence of SEQ ID NO: 25407;
   (b) a polynucleotide encoding a polypeptide having the amino acid sequence of SEQ ID NO: 1720;
   (c) a polynucleotide having at least 90% sequence identity to the polynucleotide of (a) or (b), and encoding a functional homolog of said polypeptide having the amino acid sequence of SEQ ID NO: 1720; and
   (d) a polynucleotide encoding a polypeptide having at least 90% sequence identity to a polypeptide having the amino acid sequence of SEQ ID NO: 1720, wherein said encoded polypeptide is a functional homolog of said polypeptide having the amino acid sequence of SEQ ID NO: 1720, wherein expression of said recombinant DNA construct increases yield.

2. A transgenic plant comprising a recombinant DNA construct, wherein said construct comprises a promoter functional in a plant cell, wherein said promoter is positioned to provide for expression of a polynucleotide encoding a polypeptide, and wherein said polynucleotide is selected from the group consisting of:
   (a) a polynucleotide comprising the nucleic acid sequence of SEQ ID NO: 25407;
   (b) a polynucleotide encoding a polypeptide having the amino acid sequence of SEQ ID NO: 1720;
   (c) a polynucleotide having at least 90% sequence identity to the polynucleotide of (a) or (b), and encoding a functional homolog of said polypeptide having the amino acid sequence of SEQ ID NO: 1720; and
   (d) a polynucleotide encoding a polypeptide having at least 90% sequence identity to a polypeptide having the amino acid sequence of SEQ ID NO: 1720, wherein said encoded polypeptide is a functional homolog of said polypeptide having the amino acid sequence of SEQ ID NO: 1720, wherein expression of said recombinant DNA construct increases yield.

3. The transgenic plant according to claim 2, wherein said plant is a crop plant.

4. The transgenic plant according to claim 3, wherein said plant is maize.

5. The transgenic plant according to claim 3, wherein said plant is soybean.

6. The transgenic plant according to claim 2, wherein said plant is soybean, cotton, canola, wheat, sunflower, sorghum, alfalfa, barley, millet, rice, tobacco, a fruit, a vegetable, or turf grass plant.

7. The transgenic plant according to claim 2, wherein said polynucleotide having at least 90% sequence identity to the polynucleotide of (a) or (b) has at least about 95% sequence identity with SEQ ID NO: 25407.

8. The transgenic plant according to claim 2, wherein said polynucleotide having at least 90% sequence identity to the polynucleotide of (a) or (b) has at least about 98% sequence identity with SEQ ID NO: 25407.

9. The transgenic plant according to claim 2, wherein said polynucleotide is a polynucleotide encoding a polypeptide having the amino acid sequence of SEQ ID NO: 1720.

10. The recombinant DNA construct according to claim 1, wherein said polynucleotide is a polynucleotide encoding a polypeptide having the amino acid sequence of SEQ ID NO: 1720.

11. The transgenic plant according to claim 2, wherein said encoded polypeptide has at least 95% sequence identity to SEQ ID NO: 1720.

12. The transgenic plant according to claim 2, wherein said functional homolog provides 1,4-alpha-glucan branching enzymatic activity.

13. The transgenic plant according to claim 2, wherein said functional homolog comprises one or more conservative amino acid substitutions in SEQ ID NO: 1720.

14. The transgenic plant according to claim 2, wherein said promoter comprises a tissue specific enhancer.

15. The transgenic plant according to claim 2, wherein said polynucleotide further encodes a transit peptide for targeting to a plastid.

* * * * *